United States Patent
Tsourkas et al.

(10) Patent No.: US 9,631,218 B2
(45) Date of Patent: Apr. 25, 2017

(54) SORTASE-MEDIATED PROTEIN PURIFICATION AND LIGATION

(71) Applicant: THE TRUSTEES OF THE UNIVERSITY OF PENNSYLVANIA, Philadelphia, PA (US)

(72) Inventors: Andrew Tsourkas, Bryn Mawr, PA (US); Robert Warden-Rothman, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/774,986

(22) PCT Filed: Mar. 17, 2014

(86) PCT No.: PCT/US2014/030208
§ 371 (c)(1),
(2) Date: Sep. 11, 2015

(87) PCT Pub. No.: WO2014/145441
PCT Pub. Date: Sep. 18, 2014

(65) Prior Publication Data
US 2016/0032346 A1  Feb. 4, 2016

Related U.S. Application Data

(60) Provisional application No. 61/799,379, filed on Mar. 15, 2013.

(51) Int. Cl.
C12P 21/06 (2006.01)
C07K 1/22 (2006.01)
C12P 21/02 (2006.01)

(52) U.S. Cl.
CPC ............ *C12P 21/06* (2013.01); *C07K 1/22* (2013.01); *C12P 21/02* (2013.01); *C07K 2319/21* (2013.01)

(58) Field of Classification Search
None
See application file for complete search history.

(56) References Cited

U.S. PATENT DOCUMENTS 7,238,489 B2    7/2007   Schneewind et al.
2014/0030697 A1  1/2014   Ploegh et al.

FOREIGN PATENT DOCUMENTS

WO    WO 2005/051976 A2 *  6/2005
WO    WO 2012/142659      10/2012
WO    WO 2013/003555       3/2013

OTHER PUBLICATIONS

Warden-Rothman et al., "Sortase-tag expressed protein ligation: combining protein purification and site-specific bioconjugation into a single step", Anal. Chem. Oct. 2013, 85(22): 11090-7.

\* cited by examiner

*Primary Examiner* — Amber D Steele
*Assistant Examiner* — Schuyler Milton
(74) *Attorney, Agent, or Firm* — Mark S. Cohen; Pearl Cohen Zedek Latzer Baratz LLP

(57) ABSTRACT

The invention relates to a sortase-mediated protein purification and ligation. Specifically, the invention relates to a technique that links protein expression/purification with conjugation to therapeutic agents, imaging agents, or linkers.

16 Claims, 9 Drawing Sheets

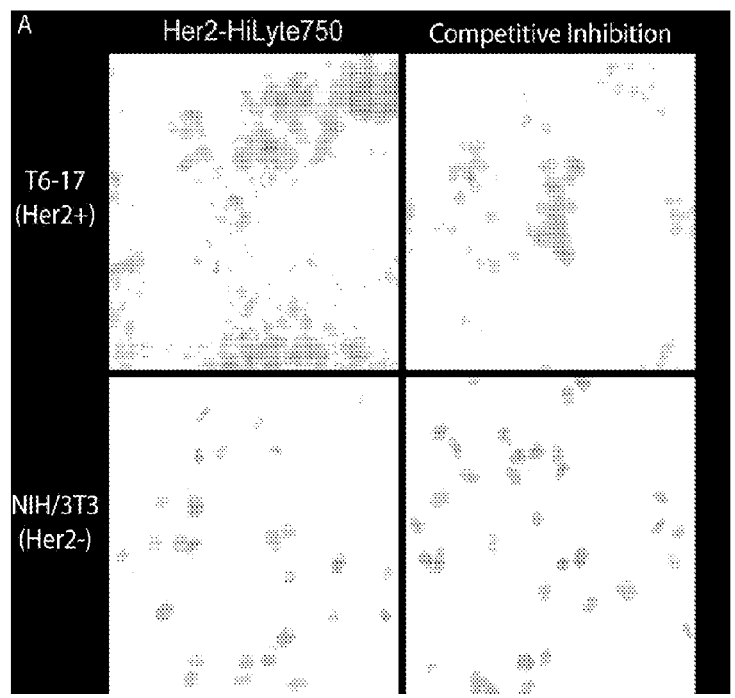
FIGURE 7A
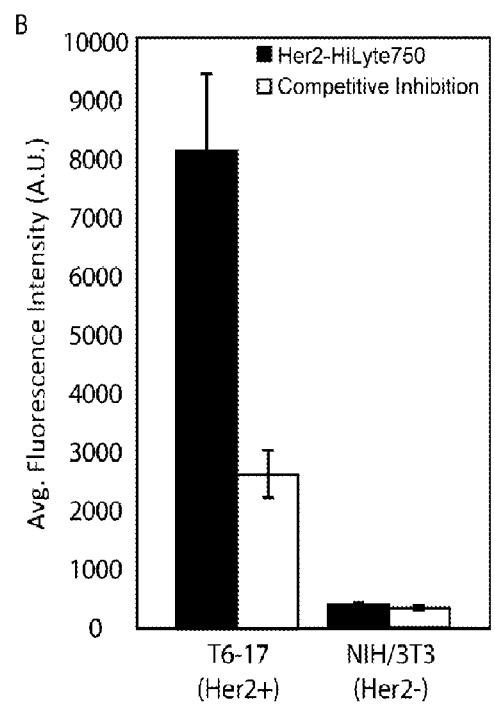
FIGURE 7.B

SORTASE-MEDIATED PROTEIN PURIFICATION AND LIGATION

CROSS-REFERENCE TO RELATED APPLICATIONS

This application is a National Phase Application of PCT International Application No. PCT/US14/30208, International filing date Mar. 17, 2014, which claims priority to and the benefit of U.S. Provisional Patent Application 61/799,393, filed Mar. 15, 2013, all of which are incorporated by reference herein in their entirety.

GOVERNMENT INTEREST STATEMENT

This invention was made with government support under grant numbers R01 EB012065 and R01 CA157766 awarded by the National Institutes of Health. The government has certain rights in the invention.

FIELD OF THE INVENTION

The invention relates to sortase-mediated protein purification and ligation. Specifically, the invention relates to techniques that link protein purification with conjugation to other agents, including therapeutic agents, imaging agents, or linkers.

BACKGROUND OF THE INVENTION

Molecular imaging and targeted therapeutic research relies heavily on affinity ligands that can seek out and bind to particular cell surface markers. These targeting ligands allow specific populations of cells to be tracked and quantified in vivo. A targeting ligand's utility lies in its ability to direct a therapeutic or imaging moiety to the targeted cells.

A number of methods have been developed to link a ligand to its cargo, based on maleimide, N-hydroxysuccinimide, carbodiimide, and click chemistries. However, many of these suffer from poor reaction efficiencies and all of them label at random residues on the ligand. Random labeling is problematic because a poorly placed conjugate can greatly reduce a ligand's affinity for its target. Additionally, ligands may receive any number of conjugates, eliminating their ability to be quantitative or stoichiometric. A few techniques have been developed to address these problems, but they have shortcomings of their own. First, expressed protein ligation (EPL) is a technique developed to attach a short synthetic peptide with orthogonal biochemistry to the N or C-terminus of a bacterially expressed protein. Unfortunately, EPL's dependence on thioesters prohibits using the technique with proteins that contain disulfides, a significant limitation. Another problem with EPL is that the ligated and unligated proteins cannot usually be separated, requiring the cheaply expressed protein to be the limiting reactant during labeling instead of the expensive synthetic peptide.

Sortase has already been used recently for a number of protein engineering tasks, including protein purifications. By placing an LPXTG motif between SrtA and a protein of interest (SrtA is upstream of the protein in this case—i.e. at the N-terminus), a calcium triggered self-cleaving peptide can be created, leaving only an N-terminal glycine behind on the protein of interest. Another common use of SrtA involves expressing a protein of interest with a C-terminal LPXTG tag. The transpeptidase is then used to link a short peptide beginning with glycine and containing a fluorophore or other unnatural moiety to the protein. However, all reported cases to date require the addition of sortase, i.e. it is not cloned into the vector, so the sortase enzyme must be purified from the ligand, adding further inefficiency. This conjugation technique also requires the purified protein to be the limiting reactant.

Accordingly, there exists a need for improved techniques for protein purification and conjugation.

SUMMARY OF THE INVENTION

According to one aspect of the invention, provided herein is a nucleic acid conjugate comprising: a coding sequence of a ligand in series with a coding sequence of sortase recognition, a coding sequence of sortase (e.g., sortase A), and a coding sequence of an affinity tag. Also provided herein is a vector comprising said nucleic acid conjugate. Further provided herein is a protein encoded by said nucleic acid conjugate.

According to another aspect of the invention, provided herein is a conjugation method comprising: cloning a coding sequence of a ligand in series with a coding sequence of sortase recognition, a coding sequence of sortase (e.g., sortase A), and a coding sequence of an affinity tag; expressing and purifying the protein; and adding calcium and a peptide or protein with an N-terminal glycine, wherein the addition of said calcium and said peptide or protein with an N-terminal glycine allows the sortase to catalyze ligand release and conjugation of the released ligand to said peptide or protein with an N-terminal glycine.

In an exemplary embodiment, the sortase recognition sequence comprises LPXTG. Any suitable affinity tag can be used. In one example, the affinity tag is histidine tag.

The peptide or protein with an N-terminal glycine may comprise a functional group. The peptide or protein with an N-terminal glycine can be linked to any agent or molecule, including, for example, but not limited to, a drug molecule, an imaging agent, a click chemistry group (e.g., an alkyne or an azide), a hapten (e.g., biotin), a protein, a small molecule, and a nanoparticle.

In a preferred embodiment, the peptide or protein with an N-terminal glycine comprises a plurality of N-terminal glycines.

According to one aspect of the invention, provided herein is a method for purifying a protein, the method comprising: cloning a coding sequence of a ligand protein in series with a coding sequence of sortase recognition, a coding sequence of sortase (e.g., sortase A), and a coding sequence of an affinity tag; expressing and purifying the protein; and adding calcium and a peptide or protein with an N-terminal glycine, wherein the addition of said calcium and said peptide or protein with an N-terminal glycine allows the sortase to catalyze ligand release and conjugation of the released ligand to said peptide or protein with an N-terminal glycine.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 7. Functional evaluation of the Her2 affibody-HiLyte Fluor™ 750 conjugate. (A) Her2/neu positive and negative cells were incubated with Her2/neu-targeted affibodies that were conjugated to HiLyte Fluor™ 750 (red) using the STEPL system. Cells were also stained with Hoechst 33342 (nuclear stain, blue). (B) In-cell western quantification of HiLyte Fluor™ 750 fluorescence.

DETAILED DESCRIPTION OF THE INVENTION

Figure 1:
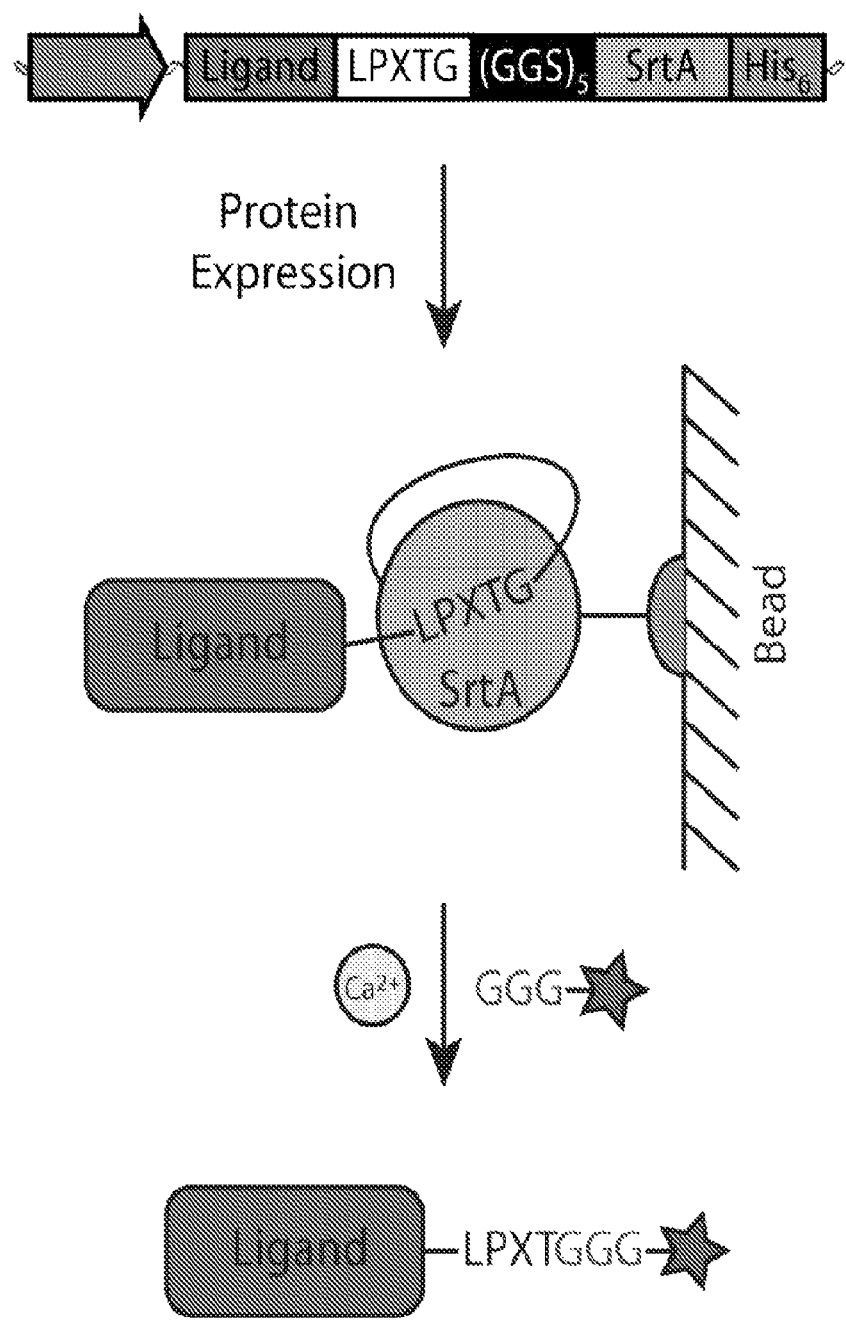
FIG. 1. Sortase Expressed Protein Ligation Scheme. Ligands are cloned in series with the amino acid sequence LPXTG, a (GGS)$_5$ linker, SrtA and a hexahistidine tag, respectively. The chimeric protein is expressed and isolated on a nickel column. The addition of calcium and a peptide with an N-terminal glycine (and optimally 3 glycines) allows the SrtA enzyme to simultaneously catalyze ligand release and peptide ligation. This allows any cargo (e.g. a fluorophore, azide, biotin, PEG, proteins, etc.—represented by the star) that is attached to the triglycine peptide to be site-specifically conjugated to the ligand.

The invention relates to a sortase-mediated protein purification and ligation. Specifically, the invention relates to a technique that links protein expression/purification with conjugation to therapeutic agents, imaging agents, or linkers.

Combining the concepts behind expressed protein ligation (EPL) with a sortase enzyme, the inventors of the instant application have developed a technique that links protein expression/purification with conjugation to therapeutic agents, imaging agents, or linkers that can be used for subsequent conjugations (e.g. biotin, click chemistry groups such as azides or alkynes). Specifically, the coding sequence for the desired protein (e.g. a targeting ligand) is cloned in series with the coding sequence for a sortase recognition sequence (e.g. LPXTG) followed by Sortase A and an affinity tag (e.g. Histidine Tag).

Accordingly, in one aspect, the invention provides a nucleic acid conjugate comprising: a coding sequence of a ligand in series with a coding sequence of sortase recognition, a coding sequence of sortase (e.g., sortase A), and a coding sequence of an affinity tag. Also provided herein is a vector comprising said nucleic acid conjugate. Further provided herein is a protein encoded by said nucleic acid conjugate.

In a preferred embodiment, the sortase recognition sequence includes the motif LPXTG (Leu-Pro-any-Thr-Gly—SEQ ID NO: 1) (wherein the occurrence of X represents independently any amino acid residue). Sortase cleaves between the Gly and Thr of the LPXTG motif. Other variant sortase recognition sequences, known in the art, can also be used. Variant sortase recognition sequences are known and described in PCT international patent application WO 2013003555, U.S. Pat. No. 7,238,489 and U.S. Patent Application publication 20140030697, which are fully incorporated by reference herein in their entirety. Examples of other sortase recognition sequences, include, but are not limited to LPKTG (SEQ ID NO: 2), LPATG (SEQ ID NO: 3), LPNTG (SEQ ID NO: 4), LPETG (SEQ ID NO: 5), LPXAG (SEQ ID NO: 6), LPNAG (SEQ ID NO: 7), LPXTA (SEQ ID NO: 8), LPNTA (SEQ ID NO: 9), LGXTG (SEQ ID NO: 10), LGATG (SEQ ID NO: 11), IPXTG (SEQ ID NO: 12), IPNTG (SEQ ID NO: 13), IPETG (SEQ ID NO: 14). Additional suitable sortase recognition motifs will be apparent to those of skill in the art, and the invention is not limited in this respect. It will be appreciated that the terms "recognition motif" and "recognition sequence", with respect to sequences recognized by a transamidase or sortase, are used interchangeably.

The coding sequence of any sortase enzyme can be used. Sortases are well known in the art. Sortases are also referred to as transamidases, and typically exhibit both a protease and a transpeptidation activity. Sortases have been classified into 4 classes, designated A, B, C, and D; designated sortase A, sortase B, sortase C, and sortase D, respectively, based on sequence alignment and phylogenetic analysis of 61 sortases from Gram-positive bacterial genomes. In a preferred embodiment, sortase is sortase A. In some embodiments, the sortase is sortase A from *Staphylococcus aureus* or sortase A from *Streptococcus pyogenes.*

The coding sequences of sortases, including sortase A, are well known in the art and publicly available in biological sequence databases and U.S. Pat. No. 7,238,489, which are incorporated herein in their entirety.

In some embodiments, the coding sequence of sortase recognition is operably linked to the coding sequence of sortase via a linker. Any suitable linker known to one of skilled in the art can be used. In a particular embodiment, the linker is a $(GGS)_5$ linker. The $(GGS)_5$ linker facilitates the sortase domain to have the conformational freedom to recognize the sortase recognition motif.

Any affinity tag known to one skilled in the art can be used. In a particular embodiment, the affinity tag is a histidine tag.

The invention also provides a vector comprising the conjugate described herein. Any suitable expression vector known to one of skilled in the art can be used. The expression protocol can be optimized based on the chosen vector.

Following protein expression and purification, the targeting ligand can be released from the sortase and affinity tag by administration of Calcium and glycine. Peptides with one or more N-terminal glycines are preferred. During this process the glycine-peptide is specifically ligated to the C-terminus of the targeting ligand. This method therefore allows for the facile conjugation of a peptide specifically to the C-terminus of the expressed protein.

For example, the use of the peptide GGG-K(FAM) allows for the attachment of the fluorescent dye FAM to the C-terminus of the expressed protein. This dye can be ligated, for example, in a 1:1 stoichiometric ratio with the expressed protein. Therefore, it is site-specific and can be used for quantitative analysis of fluorescence.

Any molecule that can be attached to a peptide with an N-terminal glycine can be specifically attached to the C-terminus of the expressed protein (e.g. dyes, drugs, haptens such as biotin, etc.).

In one example, the inventors ligated a peptide with an azide group (e.g. GGG-K(azide)), which was subsequently used for click conjugations reactions. For example, after ligation the click chemistry could be used to attach the expressed protein onto surfaces (e.g. for ELISA assays and nanoparticle surfaces) Importantly, the conjugation in this case is site-specific, so all of the proteins are oriented in the same direction on the surface. Moreover, there is only a single attachment point—the azide-which was ligated to the c-terminus of the express protein in a 1:1 ratio. One could also click drug molecules or other agents to our expressed protein, in a site-specific manner.

A general vector for bacterial expression has been produced. The expression protocol has been optimized. The cleavage reaction has been studied quantitatively and modeled to allow for optimization based on the user's needs. The system has been successfully used to express and conjugate a number of proteins including EGFP, affibodies, natural extracellular matrix binding domains, and cytokines. The conjugated peptides have included visible and near-IR fluorophores and bio-orthogonal reactive groups (e.g., azide).

In addition to calcium for cleavage, any suitable agent known to one of skilled in the art can be used. For Example, one can reengineer the sortase domain to depend on a transition metal or small molecule rather than calcium for cleavage.

The invention described herein has a number of advantages over expressed protein ligation and other sortase-mediated purification or conjugation systems. First, the invention links the final purification step to conjugation, ensuring that recovered protein is conjugated. This eliminates the difficult separation of conjugated and unconjugated peptide. Second, placing the protein of interest N-terminal to the LPXTG motif allows the first, glycine-free step in the sortase mechanism to occur without releasing any protein. Because the sortase retains the protein during this step, the crippling W194A mutation (which is required in other sortase purification techniques) is unnecessary and the more efficient wild-type Sa-SrtA can be used. Additionally, this system's single protein removes the additional step of purifying added sortase from the conjugated peptide, a common feature of sortase conjugation systems. The system also avoids chemistry based on functional groups generally found in biology, such as amines and thiols, greatly expanding the classes of proteins that can be expressed.

The invention can be used in recombinant protein expression and several other applications. These applications include, for example, efficient and economic production of targeting ligands to deliver imaging and therapeutic agents for many diseases. Due to the 1:1 nature of ligand to conjugate, it could also be used for quantitative flow cytometry. Another use is PEGylation of a biologic drug to help improve circulation time. Additionally, one of the most important uses is the ability to ligate unique chemical moieties (e.g. click groups such as azides or alkynes, biotin, DIG, etc), at the c-terminus of the expressed protein that allows for facile and site-specific conjugation to surfaces, drugs, imaging agents, nanoparticles, etc.

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

EXAMPLES

Example 1

Sortase-Tag Expressed Protein Ligation (STEPL): Combining Protein Purification and Site-Specific Bioconjugation into a Single Step In this study, a bacterial sortase enzyme was utilized to condense targeting ligand purification and site-specific conjugation at the C-terminus into a single step. A model was produced to determine optimal reaction conditions for high conjugate purity and efficient utilization of cargo. As proof-of-principle, the sortase-tag expressed protein ligation (STEPL) technique was used to generate tumor-specific affinity ligands with fluorescent labels and/or azide modifications at high purity (>95%) such that it was not necessary to remove unconjugated impurities. Click chemistry was then used for the highly efficient and site-specific attachment of the azide-modified targeting ligands onto nanoparticles.

We have created a single protein construct with the amino acid sequence LPXTG, a (GGS)$_5$ linker, SrtA, and a His-tag, respectively, fused to the C-terminal end of the protein of interest (FIG. 1). This sortase-tag expressed protein ligation (STEPL) technique links protein purification and conjugation into a single step. The flexible (GGS)$_5$ linker gives the sortase domain the conformational freedom to recognize the LPXTG in a unimolecular reaction. Addition of calcium and any protein/peptide with an N-terminal glycine (and attached cargo, if desirable) activates the sortase domain, ligating the protein of interest to the peptide while simultaneously cleaving it from the rest of the sortase chimera. Thus the conjugate is released while the sortase enzyme is retained on the column via the His-tag. By making purification and conjugation codependent, STEPL remains site-specific and stoichiometric in nature, but does not require any additional steps to remove SrtA from the purified protein sample. Further, large excesses of peptide are not essential since only correctly ligated product is released from the affinity column and conditions can be optimized to nearly exhaust any added peptide. In this study, the STEPL protocol is optimized, modeled, and used to conjugate the Her2/neu and EGFR-targeting affibody to fluorophores for imaging and/or an azide for subsequent copper-free click chemistry reactions with azadibenzocyclooctyne (ADIBO)-functionalized superparamagnetic iron oxide nanoparticles, demonstrating the system's flexibility, efficacy, and utility.

Experimental Procedures

Cloning.

Sa-SrtAΔ59 was amplified from pGMBCS-SrtA (Addgene plasmid 21931) with an N-terminal (GGS)$_5$ sequence and C-terminal H$_6$ sequence. To facilitate blue/white screening, the Lac operon was amplified from pUC19 (Invitrogen) in an antisense orientation with a C-terminal sequence coding for the restriction site XhoI, the sortase recognition sequence LPETG, and the (GGS)$_5$ linker. Overlap-extension PCR was used to join the Lac operon product to the Sa-SrtAΔ59 product. The full sequence was then cloned into pRSET-A (Invitrogen) via the NdeI and MluI restriction sites, creating the STEPL vector, pSTEPL. Sequences were verified by restriction analysis and sequencing. The Her2/neu affibody sequence and the EGFR sequence were amplified with 5' NdeI and 3' SalI sites and cloned into pSTEPL via its NdeI and XhoI sites. White colonies were picked and verified by restriction analysis and sequencing.

Notably, five GGS repeats were chosen for this fusion construct because the crystal structure reports a length of 26.2 Å between the N-terminus of the sortase domain and its active site, corresponding to the length of approximately 3 GGS repeats (8.8 Å each). Thus a (GGS)$_5$ linker was expected to provide sufficient spatial flexibility for the sortase domain to recognize and bind the LPXTG motif.

Protein Expression, Cleavage, & Bioconjugation.

Constructs were transformed into the BL12-derived Rosetta2 BL21(DE3) line (EMD Millipore). 50 mL starter cultures were grown overnight in LB-Ampicillin. These were added to 450 mL of LB and grown to an OD600 of 0.8-1 before induction with 0.5 mM Isopropyl β-D-1-thiogalactopyranoside (IPTG). Cultures were allowed to express for 24 hrs at 25° C. Cells were then harvested by centrifugation (6000 RPM, 15 min) and resuspended in 10 mL of lysis buffer (50 mM NaH$_2$PO$_4$, 300 mM NaCl, 1 mg/mL Lysozyme, 1 EDTA-free cOmplete Mini protease inhibitor tablet (Roche), pH 7.5). Lysates were incubated at room temperature for 30 min under gentle agitation before freezing overnight at −80° C. Samples were then thawed and incubated for 30 min with DNAse I (Roche) under gentle agitation. Lysates were then sonicated and separated by centrifugation (10,000 rpm, 30 min).

For optimization experiments, 8 mL of clarified lysate for each condition was incubated for 1 hr with 0.6 mL Talon resin (Clontech, equilibrated in lysis buffer). The lysate and beads were then added to a column and beads were washed with 6 mL STEPL buffer (20 mM Tris-base, 50 mM NaCl, pH 7.5). Washed beads were resuspended in a total of 1.2 mL of STEPL buffer containing the indicated amounts of CaCl$_2$ and triglycine (Sigma-Aldrich) and aliquoted into three 1.5 mL microcentrifuge tubes. Samples were shaken at 1,000 rpm, the indicated temperature, and protected from light. At each timepoint, samples were spun down at 3,000 rpm for 5 min Absorbance spectra were taken of the supernatants from 400-600 nm using a Cary 100 Bio UV-Visible Spectrophotometer (Varian) and the sample was returned to shaking. At the end of the timecourse, beads were washed three times with 1 mL STEPL buffer and incubated for 30 min in 100 mM EDTA. Stripped beads were spun down as before and the absorbance spectra were taken of the supernatants from 400-600 nm.

For bioconjugation experiments, 8 mL of clarified lysate was incubated for 1 hr with 0.5 mL Talon resin (equilibrated in lysis buffer). The lysate and beads were added to a column and beads were washed with 5 mL STEPL buffer. 400 μL of STEPL buffer containing 150 μM synthetic peptide (Table 2) or 5 mM triglycine (for labeled and unlabeled preparations, respectively) and 100 μM CaCl2 was flowed over the beads until it replaced the wash buffer. Columns were protected from light and reacted for 6 hrs at 37° C. 1 mL of STEPL buffer was added to the column and the flowthrough collected. To remove unreacted peptide, flowthrough was dialyzed three times against 4 L of STEPL buffer at 4° C. while protected from light (Slide-A-Lyzer2 cassettes, 3.5K cutoff, Thermo Scientific).

EGFP Release Analysis & Model Design.

Absorbance spectra obtained from optimization samples were baseline corrected and the EGFP concentration was determined using the Beer-Lambert law ($\epsilon$(EGFP, 488 nm)=55,000 M$^{-1}$ cm$^{-1}$. EGFP concentrations were fit to the sum of equations 4 and 5 in the following system of ODEs using non-linear least squares:

$$\frac{d[EGFP \cdot SrtA]}{dt} = -k_1[EGFP \cdot SrtA] - k_2[EGFP \cdot SrtA][GGG] \quad (1)$$

$$\frac{d[SrtA]}{dt} = k_1[EGFP \cdot SrtA] + k_2[EGFP \cdot SrtA][GGG] \quad (2)$$

$$\frac{d[GGG]}{dt} = -k_2[EGFP \cdot SrtA][GGG] \quad (3)$$

$$\frac{d[EGFP]}{dt} = k_1[EGFP \cdot SrtA] \quad (4)$$

$$\frac{d[EGFP \cdot GGG]}{dt} = k_2[EGFP \cdot SrtA][GGG] \quad (5)$$

$$k_1 = A_1 T e^{-\Delta G_1^\ddagger / RT} \quad (6)$$

$$k_1 = A_2 T e^{-\Delta G_2^\ddagger / RT} \quad (7)$$

where the model fits for $A_1$, $A_2$, $\Delta G_1^\ddagger$, and $\Delta G_2^\ddagger$. Temperatures are on the Kelvin scale. Initial EGFP·SrtA concentration was determined by adding the concentration of EGFP in the final timepoint to the concentration of EGFP from the stripped beads. Initial triglycine concentration and temperature were varied experimentally. Initial conditions for SrtA, EGFP, and EGFP·GGG were zero. Model predictions were produced with the following initial conditions: 100 μM $Ca^{2+}$, 100 μM EGFP·SrtA, 1 μM-1 mM triglycine, 4°-37° C.

Cell Culture.

NIH/3T3 and T6-17 cells (i.e. NIH/3T3 cells engineered to stably express the Her2/neu receptor; kindly provided by Dr. Mark Greene, University of Pennsylvania) were maintained in Dulbecco's modified Eagle's medium (DMEM) supplemented with 10% fetal bovine serum, 1% penicillin/streptomycin at 37° C. and 5% CO2. H1666 cells expressing pLKO.shCTRL and pLKO.shEGFR (kindly provided by Dr. Matthew Lazzara, University of Pennsylvania) were maintained in RPMI supplemented with 10% fetal bovine serum, 1% penicillin/streptomycin at 37° C. and 5% CO2.

Fluorescence Analysis of Cell Targeting.

NIH/3T3 and T6-17 cells were incubated with 1 μM Her2/neu affibody conjugated to HiLyte Fluor 750 for 4 hours in full media with and without a 10-fold excess of unlabeled Her2/neu affibody. Cells were washed 3 times with affibody-free media before being imaged in serum-free DMEM. Imaging was performed with an Olympus IX81 inverted fluorescent microscope with a back-illuminated EMCCD camera (Andor) and a SOLA excitation source (Lumencor). Images of HiLyte Fluor 750 were acquired using the filter set (HQ710/75, HQ810/90, Q750LP) (Chroma). A LUC PLAN FLN 40× objective (NA 0.6) was used for all imaging studies. ImageJ was used to merge the fluorescent images and equalize levels. After optical imaging, the plate was scanned by an Odyssey Imaging System (Li-Cor). User-defined regions of interest were drawn within each well and fluorescence within the 800-channel was quantified to determine relative Her2/neu expression.

MR Relaxation Measurements of Cell Targeting and MR Imaging.

Azodibenzocyclooctyne (ADIBO)-functionalized superparamagnetic iron oxide (SPIO) nanoparticles were synthesized as previously described. Azide-modified Her2/neu-targeted affibody were conjugated to ADIBO-SPIO nanoparticles by combining 5 mg Fe/mL SPIO nanoparticles with 30 μM affibody. Reactions were mixed overnight at room temperature and affibody-SPIO conjugates were purified on PD-10 columns (GE Healthcare).

T6-17 and NIH/3T3 cells were incubated with 125 μg Fe/mL of Her2/neu-targeted SPIO for 45 minutes in full media with and without a 100-fold excess of unlabeled Her2/neu affibody in triplicate. Cells were transferred to 1.5 mL microcentrifuge tubes and washed with 500 μL PBS three times before being resuspended in 300 μL RIPA Lysis Buffer (Millipore). T2 measurements were taken using a benchtop relaxometer (Bruker mq60). Following relaxation measurements, cell lysates were combined 100 μL transferred to wells of a 364-well plate. Images of the cells were taken on a 9.4-T magnet interfaced to a Varian INOVA console using a 70 mm inner diameter volume coil for radiofrequency transmission and reception. T2*-weighted gradient echo (GRE) MR images were collected using parameters as follows: repetition time (TR)=200 ms, echo time (TE)=5 ms, flip angle=20°, slice thickness=0.5 mm, number of acquisitions=8.

Results

Optimization of STEPL.

A valuable feature of the STEPL system is that it allows for the site-specific labeling of recombinantly expressed proteins without requiring any steps in addition to what is normally required for protein purification. Under optimal conditions, all of the recombinant protein that is released from the affinity column would be labeled with the desired cargo as a result of the SrtA-mediated ligation reaction. To evaluate the efficiency of this ligation reaction and to assess the extent of any non-specific cleavage of the LPXTG motif, in the absence of ligation, a model system was designed with EGFP as the "ligand" (EGFP-STEPL). This allowed for quantitative monitoring of protein release from the affinity column in the presence and absence of triglycine and calcium. Notably, peptides with two or more glycines are typically preferred for SrtA-mediated ligations since they exhibit significantly improved binding and catalysis.

Figure 2:
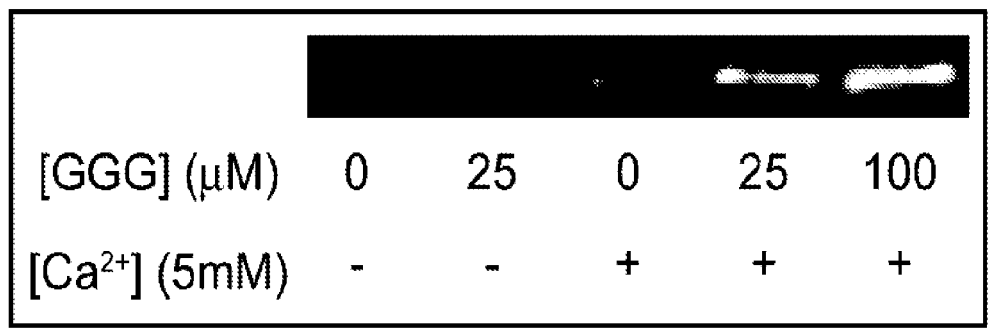
FIG. 2. Western Blot of GFP released from an affinity column under various conditions. A GFP-STEPL fusion protein was expressed and washed on an affinity column. The column was then treated with various concentrations of triglycine and Ca$^{2+}$. Released GFP was detected by western blot.
Figure 3:
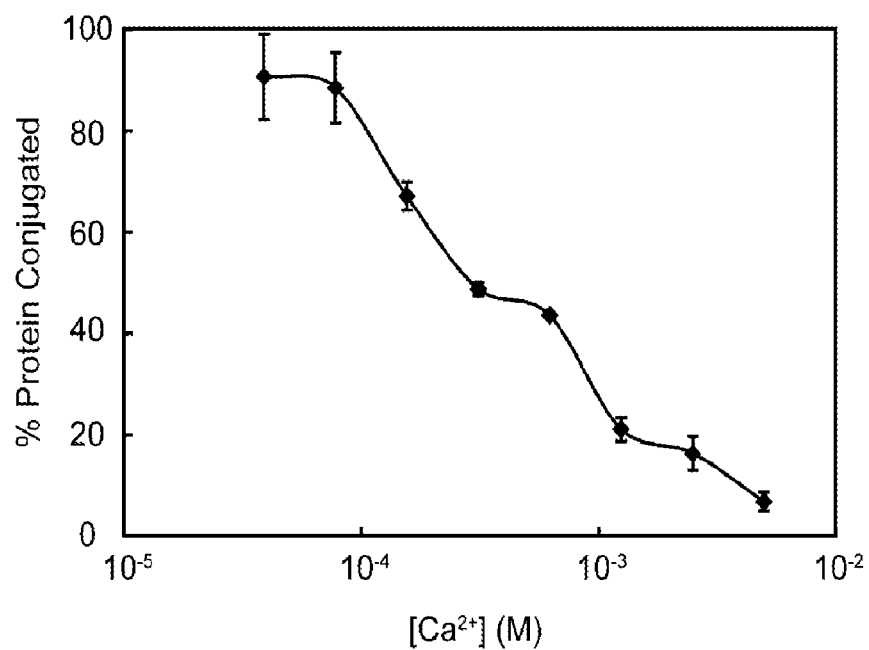
FIG. 3. Effect of calcium on the efficiency of protein ligation. A GFP-STEPL fusion protein was expressed and washed on an affinity column. The column was then treated with various concentrations of Ca$^{2+}$, in the presence of triglycine, at 37° C. for 4 hrs. These experiments provided a measure of the total amount of ligated and unligated product ($[GFP]_{Total}$) released from the affinity column for each Ca$^{2+}$ concentration. The amount of unligated product ($[GFP]_{unligated}$) was determined by performing analogous experiments in the absence of triglycine. The percent protein conjugated ($[GFP]_{ligated}$) was then calculated as ($[GFP]_{Total}$−$[GFP]_{unligated}$)/($[GFP]_{Total}$)*100.

Initial studies with the EGFP-STEPL system, in the presence and absence of $Ca^{2+}$ (5 mM) and triglycine ([GGG], 25 μM or 100 μM), revealed that release of the GFP from the affinity column increased with triglycine concentration (FIG. 2). However, it was also observed that $Ca^{2+}$ alone could lead to some non-specific release of GFP, albeit at lower levels than when triglycine was also present. In the absence of $Ca^{2+}$, no GFP was released from the affinity column, with or without triglycine. These results suggested that it was important to identify an optimal $Ca^{2+}$ concentration that would maximize the ratio of ligated (i.e. GFP-triglycine conjugates) to unligated recombinant protein. Therefore, GFP-STEPL was performed in the presence of a fixed concentration of triglycine (25 μM) and increasing concentrations of $Ca^{2+}$ (0 to 5 mM). These experiments provided a measure of the total amount of ligated and unligated product released from the affinity column for each $Ca^{2+}$ concentration. The amount of unligated product was determined by performing analogous experiments in the absence of triglycine. The maximum percent of ligated product occurred at $Ca^{2+}$ concentrations below 100 μM (FIG. 3). Therefore, a $Ca^{2+}$ concentration of 100 μM was used for all subsequent experiments.

Figure 4:
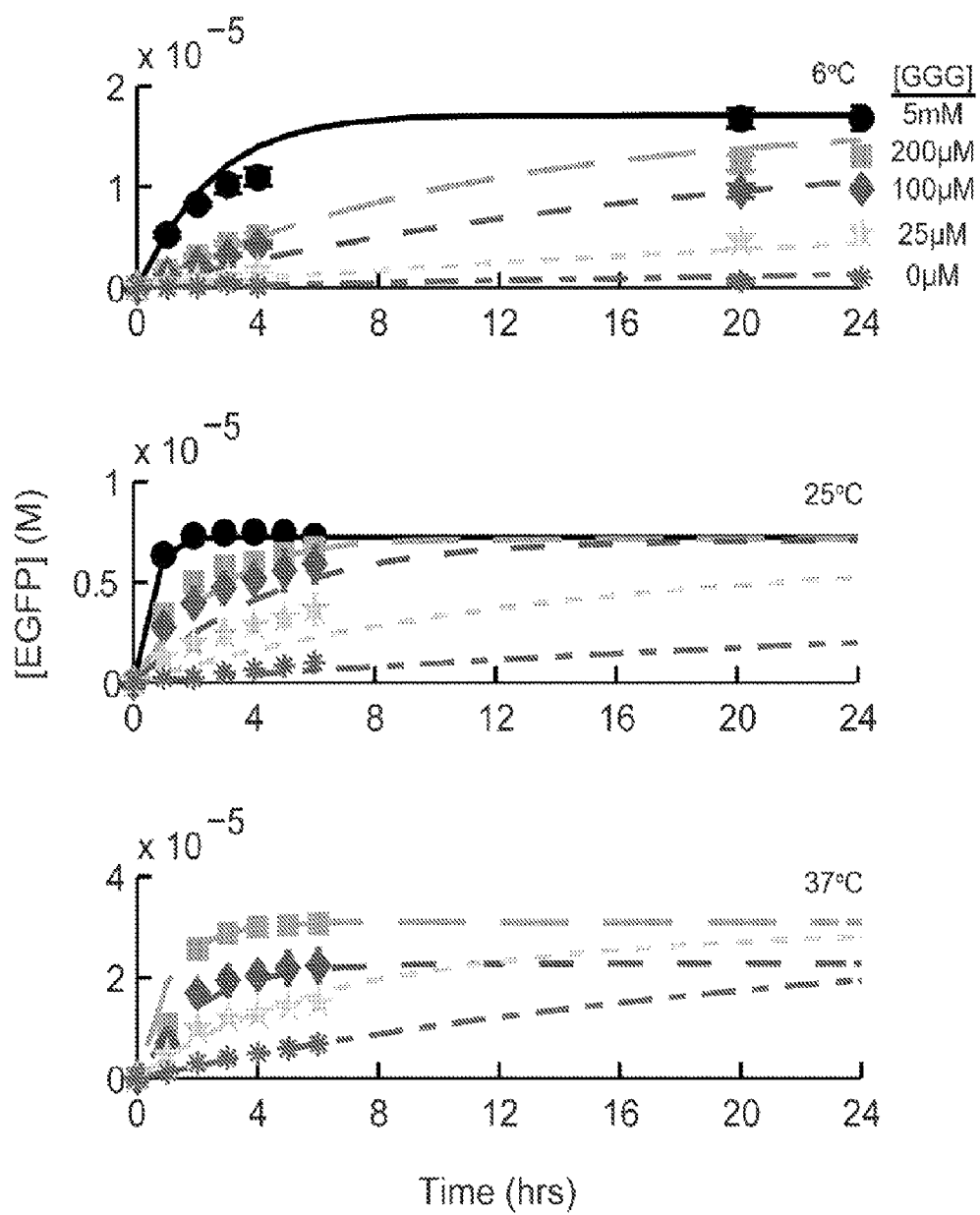
FIG. 4. Modeled and actual EGFP release from an affinity column as a function of temperature, triglycine concentration, and time. A GFP-STEPL fusion protein was expressed and washed on an affinity column. The column was then treated with 0 µM (asterisk), 25 µM (star), 100 µM (diamond), 200 µM (square), or 5 mM (circle) triglycine and 100 µM Ca2+. GFP release was monitored as a function of time. Protein release experiments were conducted at 6° C. (top), 25° C. (middle), and 37° C. (bottom). All data was fit using a kinetic model of EGFP cleavage that takes into account both triglycine-dependent and triglycine-independent pathways. Modeled GFP release (lines) has been superimposed onto the recorded data (symbols).

In order to further optimize the GFP-STEPL procedure, a systematic study on the effect of triglycine concentration, reaction temperature, and reaction time on the amount of recombinant protein released from the affinity column was conducted (FIG. 4). As expected, the rate of protein release increased with triglycine concentration and reaction temperature. All experimental data was fit with a kinetic model of the reaction, detailed in Scheme 1 below.

Scheme 1. Kinetic model of EGFP cleavage via triglycine-dependent and triglycine-independent pathways.

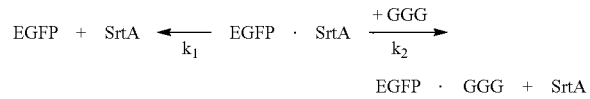

This model assumes that transpeptidation is the rate-limiting step of the glycine-dependent pathway and therefore collapses reversible peptide binding and transpeptidation into a single second-order rate constant. To include temperature dependence, the model also assumes that the rate constants can be modeled by the Arrhenius equation. Thus, the model's parameters are the preexponential constants and activation energies of the two pathways (Table 1). As shown in FIG. 4, the model provides an acceptable fit to the observed data.

TABLE 1

Model Parameters. The kinetics model determined Ahrenneous pre-exponential constants and activation energies for the glycine-free ($k_1$) and glycine-dependent pathways ($k_2$).

| Pathway | Pre-exponential Constant (A) | Activation Energy ($\Delta G^{\ddagger}$) | Rate Constant at 37° C. |
|---|---|---|---|
| Glycine-free | $4.0568 \times 10^2$ s$^{-1}$ | $3.8463 \times 10^4$ J/mol | 0.0419 s$^{-1}$ |
| Glycine-dependent | $2.9246 \times 10^{10}$ s$^{-1}$ M$^{-1}$ | $5.4958 \times 10^4$ J/mol | 5.352 0$^3$ s$^{-1}$ M$^{-1}$ |

TABLE 2

Synthetic Peptides

| Peptide | Molecular Weight (kDa) | $\lambda_{ex}/\lambda_{em}$ (nm) |
|---|---|---|
| NH$_2$-Gly-Gly-Gly-Lys(HiLyteFlour 750)-NH$_2$ | 1,327 | 754/778 |
| NH$_2$-Gly-Gly-Gly-Lys(5-FAM)-Gly-Gly-Ser-Lys(N$_3$)-NH$_2$ | 1,030 | 492/518 |

Figure 5:
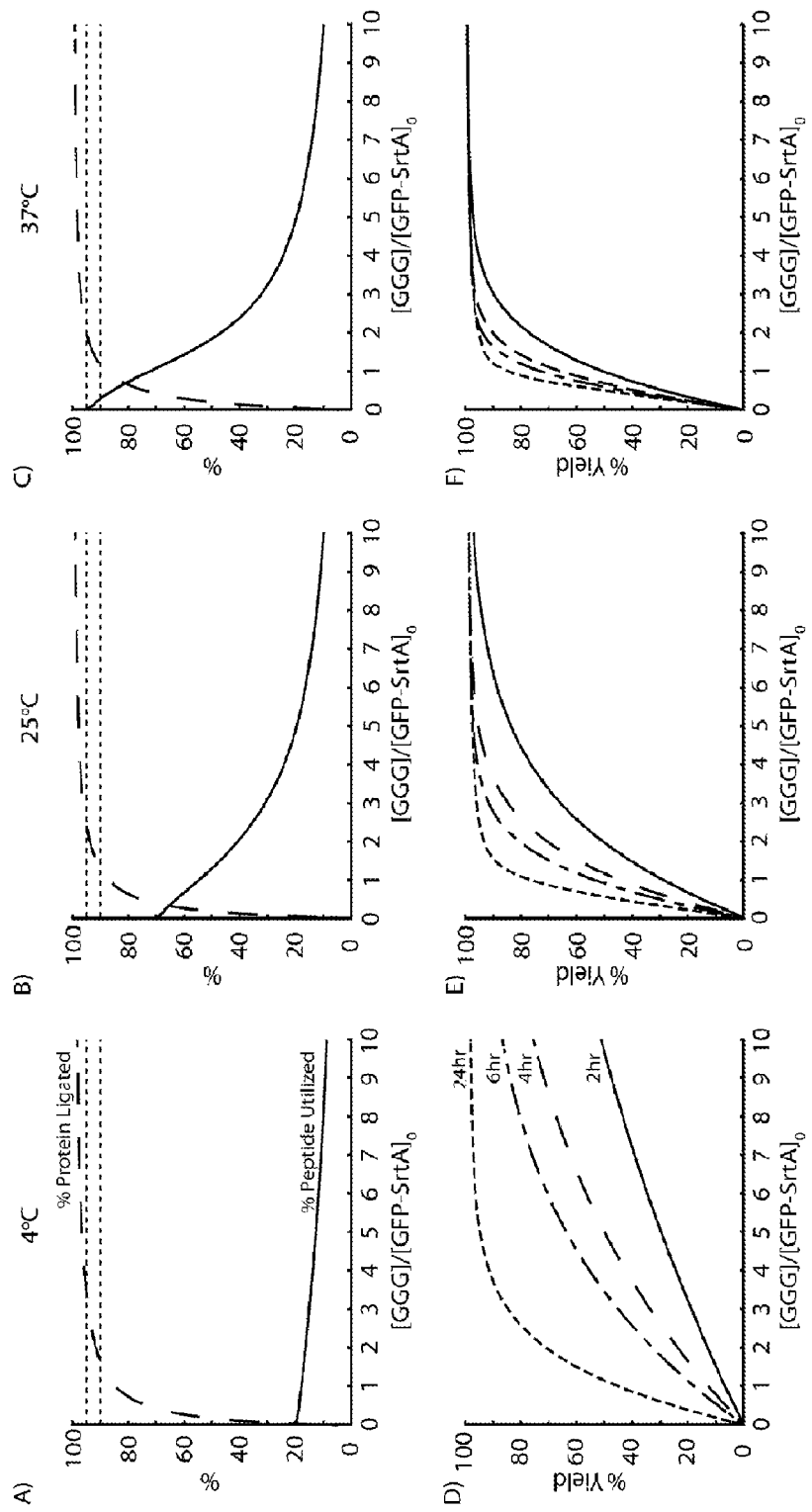
FIG. 5. Model predictions of STEPL-ligation efficiency, triglycine peptide utilization, and the percent yield of expressed GFP that is recovered from the affinity column. The kinetic model of GFP cleavage from the STEPL system was evaluated with initial conditions of 100 µM Ca$^{2+}$, 100 µM GFP-SrtA, and 1 µM to 1 mM triglycine at 4°, 25°, and 37° C. for 0 to 24 hrs. The percentage of GFP that has been ligated to triglycine (time independent) and the percentage of triglycine peptide consumed during a 6 hr incubation was determined for reaction temperatures of (A) 4° C., (B) 25° C., and (C) 37° C. Dotted lines at 90% and 95% are included for reference. The percentage of ligated GFP recovered after a 2, 4, 6, and 24 hour incubation was determined as a function of excess triglycine (relative to the total amount of GFP-SrtA) for reaction temperatures of (D) 4° C., (E) 25° C., and (F) 37° C.

The kinetic model was used to predict the effect of various reaction conditions on three outcomes: (i) the percentage of released protein that is ligated to the peptide, (ii) the percentage of peptide consumed in the reaction, and (iii) the yield of ligated protein (i.e. the amount of ligated protein normalized by the total amount of protein initially bound to the affinity column) (FIG. 5). The value for each of the desired outcomes was determined for reaction times of 2, 4, 6, and 24 h, with 100 μM CaCl$_2$, initial triglycine peptide concentrations of 1 to 1000 μM, reaction temperatures of 4, 25, or 37° C., and assuming 100 μM initial protein concentration on the affinity column. It was determined that the purity of the ligated protein was independent of reaction time, as it is simply a ratio of the two rate constants. As a result, adding excess peptide could be used to drive the ligation reaction and overwhelm the basal cleavage rate. Overall, if a highly pure ligated product is desirable, >95% purity can be achieved by simply using 2-fold or greater molar excess of triglycine-containing peptide compared with the concentration of total column-bound protein (at 37° C., FIG. 5C). This is significantly lower than the 10-fold excess of peptide typically required for efficient intein-based EPL.

If it is more desirable to exhaust all of the triglycine peptide than achieve high purity of the ligated product, perhaps because the peptide is functionalized with a cargo that is cost-prohibitive, then >90% peptide consumption can be achieved by adopting reaction conditions whereby the recombinantly expressed protein is in 4-fold or greater molar excess over the peptide (at 37° C., FIG. 5C). However, this comes at the cost of reduced purity of the ligated product and will likely require additional purification to remove unligated targeting ligands.

Higher reaction temperatures can be used to speed up the reaction and improve peptide utilization, particularly at lower triglycine peptide concentrations, but purity of the ligated product is only marginally improved. When yield is considered, the STEPL system clearly favors higher temperatures regardless of whether high purity of the ligated protein or high peptide utilization is desirable. (FIGS. 5D-F). Of course, some proteins may be unstable at high temperatures, requiring longer reactions to be performed at room temperature or in a cold room.

Fluorophore Ligation.

Figure 6:
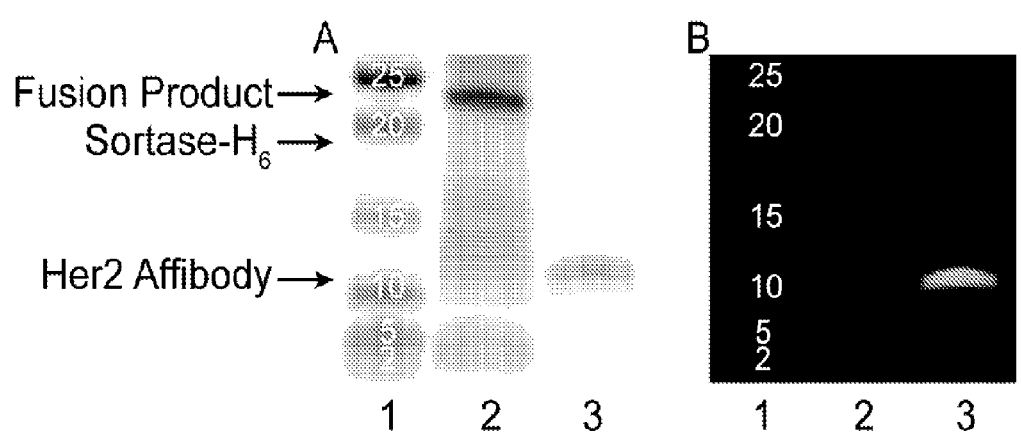
FIG. 6. Her2/neu affibody expression and ligation. An SDS-PAGE gel was run with (1) marker, (2) raw lysate of bacterially expressed STEPL-Her2 affibody, and (3) Her2 affibody purified using a 2-fold excess of HiLyte 750-labeled triglycine peptide, 100 µM Ca$^{2+}$ at 37° C. for 6 hr. (A) SimplyBlue SafeStain protein stain. (B) HiLyte 750 peptide fluorescence.
Figure 9:
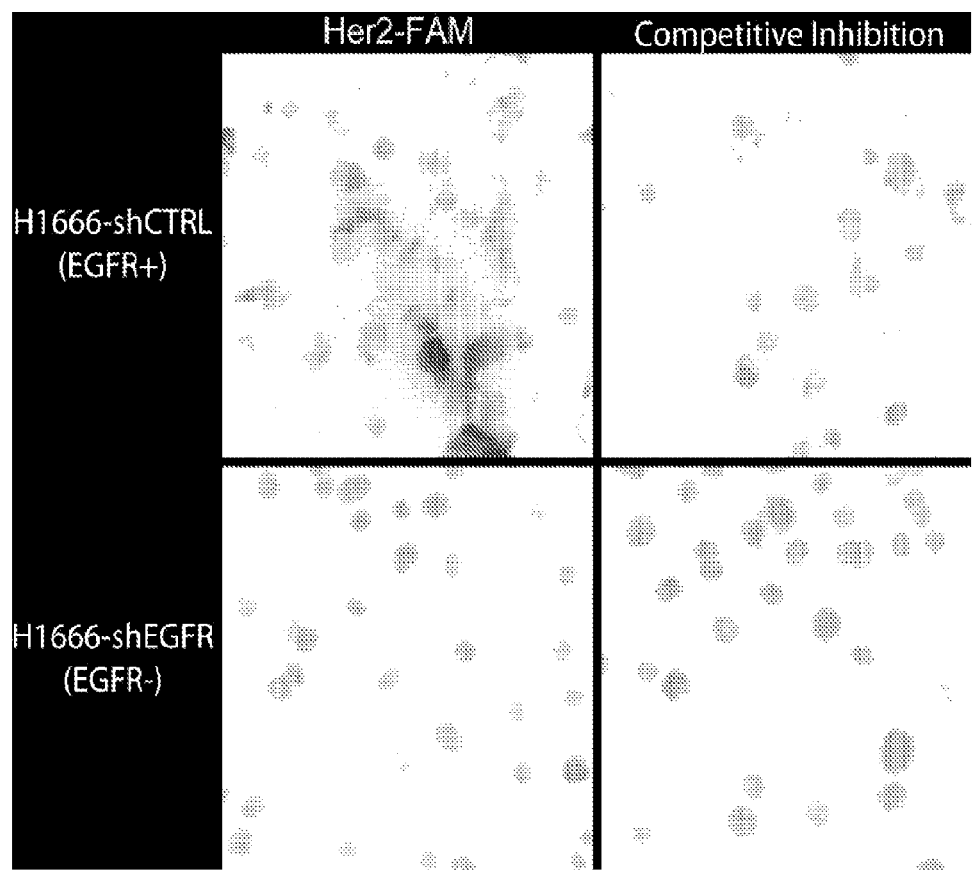
FIG. 9. Functional evaluation of the EGFR affibody-FAM conjugate. (A) EGFR-positive and -negative cells were incubated with EGFR-targeted affibodies that were conjugated to FAM (green) using the STEPL system. Cells were also stained with Hoechst 33342 (nuclear stain, blue).

To demonstrate the utility of STEPL as a general methodology for the site-specific labeling of tumor targeting ligands with imaging agents, the coding sequence for a Her2/neu-targeting affibody (Her2-affibody) was cloned into the STEPL vector. The affibody was expressed and conjugated to a triglycine peptide containing the near-infrared dye HiLyte Fluor™ 750 (Table 2) using conditions that were expected to result in >95% purity of the fluorescent labeled affibody, based on the kinetic model established above (2-fold excess peptide, 100 μM Ca$^{2+}$, 37° C., 6 hr). Efficient ligation between the affibody and the fluorescently-labeled peptide was confirmed by SDS-PAGE (FIG. 6). The major band in the 700 nm channel (protein stain) co-localized with the single fluorescent band in the 800 nm channel (HiLyte Fluor™ 750), following removal of excess free peptide by dialysis. Only a very faint signal stemming from the unligated protein was observed in the 700 nm channel, at a slightly lower molecular weight than the ligated product. To confirm that the affibody remained functional following the ligation reaction, it was incubated with T6-17 and NIH-3T3 cells in vitro, which are positive and negative for the Her2/neu receptor, respectively (FIG. 7). As expected, the affibody labeled the T6-17 cells exclusively, with no observable labeling of the NIH-3T3 cells. Further, the addition of excess unlabeled affibody (i.e. cleaved with triglycine) competitively inhibited the binding of the fluorescently labeled affibody to T6-17 cells, suggesting that binding was specific for the Her2/neu receptor. Quantification using an in-cell western assay (FIG. 7B) corroborated the fluorescence microscopy findings. Similar results were obtained by applying the epidermal growth factor receptor (EGFR)-targeted affibody to EGFR-positive and negative cells (FIG. 9).

Azide Ligation and Nanoparticle Synthesis.

Figure 8:
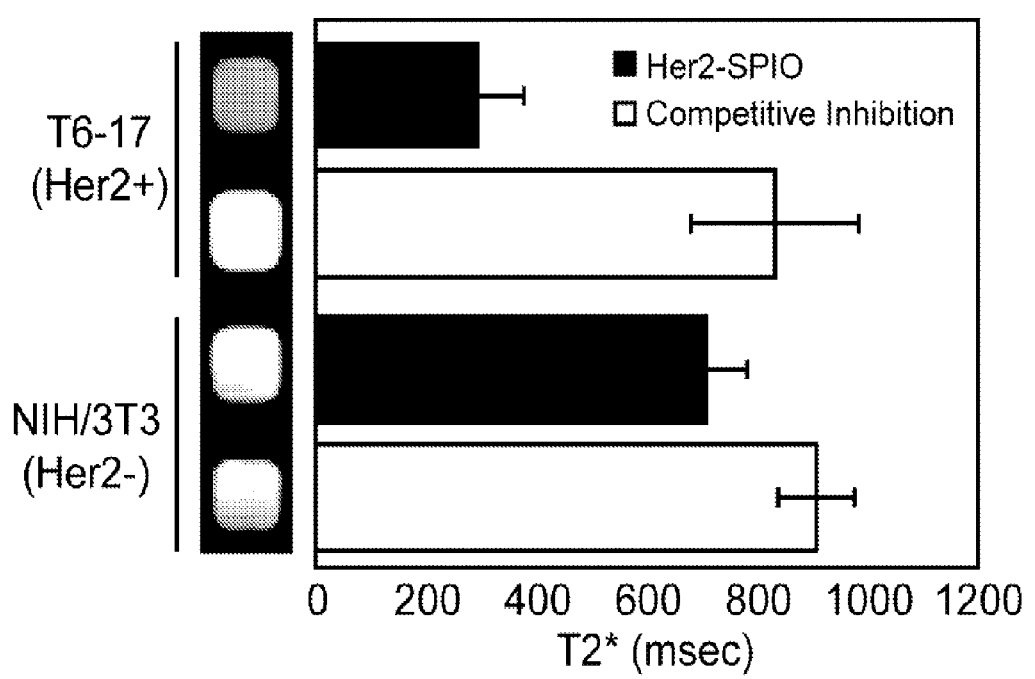
FIG. 8. Functional evaluation of the Her2 affibody-SPIO conjugates. Her2/neu-positive and Her2/neu-negative cells were incubated with Her2-SPIO conjugates in the presence and absence of excess free affibody. Free affibody served as a competitive inhibitor to confirm specific binding of the Her2/neu receptor. Relaxivity measurements and T2*-weighted MR images of each cell suspension were acquired.

In addition to imaging agents, STEPL can also be used to conjugate various other functional moieties including bio-orthogonal reactive groups (e.g. azide) onto the C-terminus of targeting ligands. The site-specific introduction of azides onto recombinant proteins provides a very favorable approach for the efficient coupling of targeting ligands to nanoparticles using click chemistry. In particular, this approach allows tight control over both ligand orientation and density on the nanoparticle surface. We have previously shown that both of these factors can have a dramatic impact on nanoparticle avidity. As proof-of-principle, the Her2/neu affibody was conjugated to a synthetic peptide containing a green fluorophore (5-FAM) as well as an azide group. This conjugate was then reacted with superparamagnetic iron oxide (SPIO) nanoparticles functionalized with azadibenzocyclooctyne (ADIBO). ADIBO is a dibenzocyclooctyne derivative capable of copper-free click reactions with azides. The resulting Her2/neu affibody-SPIO conjugates were incubated with T6-17 and NIH/3T3 cells. Cell labeling was then assessed by acquiring T2 relaxation times and T2*-weighted images of cell lysates (FIG. 8). The Her2-positive cells exhibited a marked decrease in T2-relaxation times, consistent with the presence of SPIO, in comparison to Her2-negative cells. An observable negative contrast was also observed upon MR imaging of the Her2-positive cells. Competitive inhibition, using an excess of free-unlabeled Her2-affibody, led to a loss in MR contrast, indicative of receptor-specific binding. Therefore, these results provide clear evidence that STEPL can be combined with click chemistry for the site-specific attachment of targeting ligands onto nanoparticles.

STEPL offers a number of features that make it a very favorable approach for bioconjugation reactions. First and foremost, STEPL combines release of recombinant proteins from the affinity column and bioconjugation into a single step. This greatly simplifies the entire bioconjugation procedure since no subsequent labeling and purification steps are required, saving time, money, and complexity. Second, STEPL allows for the site-specific conjugation of cargo. Site-specific functionalization has been shown to be beneficial in a number of applications including the preparation of protein-drug conjugates, which often exhibit higher efficacy than randomly labeled targeting ligands. It has also been shown that the site-specific attachment of targeting ligands to nanoparticles can improve nanoparticle avidity. Third, STEPL conjugates the peptide-to-ligand in a 1:1 stoichiometric manner. This can be important when labeling targeting ligands with imaging agents, since it allows for precise quantitative imaging. It is also beneficial for characterizing nanoparticle bioconjugations. Fourth, the conditions used to release protein from the affinity column can be manipulated to ensure that essentially all of the recovered protein is conjugated with the desired cargo. This eliminates the often-difficult process of purifying conjugated products from unconjugated proteins. Since in many applications a large protein is labeled with low molecular weight drugs or imaging agents, the conjugated and unconjugated forms of the protein can differ by as little as a few hundred to a few thousand Da, potentially without any significant change to hydrophobicity or charge. A slight excess of peptide is required to achieve complete ligation; however, excess peptide is easily removed via dialysis or gel chromatography. This purification step is analogous to the removal of imidazole from His-tagged protein samples that have been affinity purified using a nickel column Fifth, construction of the STEPL system as a single expressible protein removes the additional step of removing sortase from the conjugated product, a common feature of current sortase conjugation systems. Additionally, in systems where unconjugated ligands are easily separable from conjugated ligands, the reaction conditions could be altered to ensure that expensive synthetic peptides can be exhausted in the ligation reaction. Thus, STEPL is a single-chain, self-cleavable system where high-cost components can be fully utilized; traits highly desirable in industrial protein production as they reduce overall cost and time.

One identified shortcoming of Sortase A is that it exhibits some cleavage even in the absence of glycine. Previous studies have addressed this problem by making a destabilizing mutation to Trp-194. However, we found that reducing the calcium concentration has a similar effect with finer control, as sub-millimolar calcium concentrations provided a sharp, dose dependent drop in background cleavage. Due to the presence of cytosolic calcium in the bacterium, background cleavage may occur during protein expression; however, the calcium level inside $E.$ $coli$ is estimated to be between 0.1-1 µM. Therefore, undesirable cleavage of the fusion protein within $E.$ $coli$ is likely to be minimal and could always be further discouraged by introducing the aforementioned mutation. The size of the sortase domain is also not expected to have much effect on the yield of the fusion protein. Sortase is only 147 amino acids, less than half the size of a maltose binding domain (male), which is commonly used for affinity purification, and sortase is highly soluble.

To further optimize and understand the cleavage reaction, a kinetic model was established and its parameters (time, temperature, and initial triglycine concentration) were systematically varied. To simplify the model, the reversible binding of peptide to the enzyme and product conversion were condensed into one second-order rate constant. This is justifiable because the applicable peptide concentrations do not appear to saturate the binding curve and the determined rate constants are well below the diffusion limit, implying that product conversion is rate limiting.

The model reveals a fundamental conflict between conjugate purity and peptide utilization. The glycine-independent pathway can be easily overwhelmed by adding a large excess of peptide to drive the glycine-dependent pathway. On the other hand, the peptide can be fully utilized by making it the limiting reactant. Therefore, if product purity is required, it is optimal to use excess peptide. If peptide utilization is the primary concern, the optimal conditions are 37° C. with a 1:1 ratio (or less) of synthetic peptide to STEPL protein, although it is important to note that in this latter case additional purification is needed to purify conjugated product from unconjugated proteins. Therefore, this approach is only amenable to systems where the conjugated and unconjugated products are separable. Systems where the peptide enables the conjugate to be immobilized onto a surface or particle are ideal candidates for peptide exhaustion.

In this study, STEPL was used to functionalize affibodies with chemical groups useful for molecular imaging. A near-IR fluorophore was utilized to optically differentiate between cells expressing and lacking the proto-oncogene Her2/neu. The NIR-dyed affibody was used to quantify Her2/neu expression differences between the T6-17 and NIH/3T3 cells, which demonstrates STEPL's utility for in-cell western techniques. Additionally, the STEPL was used to conjugate a bio-orthogonal reactive group (an azide) to the Her2/neu affibody. The azide readily reacted to a strained alkyne on the surface of superparamagnetic iron oxide nanoparticles. Due to the site-specific nature of STEPL, the affibody was linked in a specific orientation, which greatly increases the particle's efficacy in distinguishing between cells expressing and lacking Her2/neu. STEPL can be used to conjugate many other moieties to its target protein, such as biotin, poly(ethylene-glycol), antibiotics, metal chelates, and photocrosslinkers, all of which have been proven compatible with the sortase enzyme.

In sum, STEPL has proven to be a flexible and efficient system for molecular imaging and targeted therapeutics. This study validated and optimized the system for ligand purity and peptide-cargo utilization. STEPL was then used to visualize and quantify Her2/neu and EGFR expression in vitro. Moreover, because it has the ability to link virtually any bacterially expressible protein with any cargo that can be attached to a triglycine peptide, STEPL has applications in many fields.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A conjugation method comprising:
cloning a nucleic acid encoding a polypeptide, the nucleic acid comprises in series from 5' to 3' a coding sequence of a ligand with a coding sequence of a sortase recognition sequence, a coding sequence of a flexible linker, a coding sequence of sortase A, and a coding sequence of an affinity tag;
expressing and purifying the polypeptide encoded by the nucleic acid; and
adding calcium and a peptide or protein with an N-terminal glycine,
wherein the addition of said calcium and said peptide or protein with an N-terminal glycine allows the sortase to catalyze ligand release and conjugation of the released ligand to said peptide or protein with an N-terminal glycine.

2. The method of claim 1, wherein said sortase recognition sequence comprises LPXTG.

3. The method of claim 1, wherein said affinity tag is a histidine tag.

4. The method of claim 1, wherein said peptide or protein with an N-terminal glycine comprises a functional group.

5. The method of claim 1, wherein said peptide or protein with an N-terminal glycine is linked to a drug molecule, an imaging agent, a click chemistry group, an alkyne, an azide, a hapten, a biotin, a protein, a small molecule, or a nanoparticle.

6. The method of claim 1, said peptide or protein with an N-terminal glycine comprises a plurality of N-terminal glycines.

7. A method for purifying a protein, the method comprising: the conjugation method of claim 1.

8. A method for purifying a protein, the method comprising:
cloning a nucleic acid encoding a polypeptide, the nucleic acid comprises in series from 5' to 3' a coding sequence of a ligand protein with a coding sequence of sortase recognition sequence, a coding sequence of a flexible linker, a coding sequence of sortase A, and a coding sequence of an affinity tag;
expressing and purifying the polypeptide encoded by the nucleic acid; and
adding calcium and a peptide or protein with an N-terminal glycine, wherein the addition of said calcium and said peptide or protein with an N-terminal glycine allows the sortase to catalyze ligand release and conjugation of the released ligand to said peptide or protein with an N-terminal glycine.

9. The method of claim 1, wherein said flexible linker comprises a glycine-serine (GS)-rich linker.

10. The method of claim 9, wherein said flexible linker comprises a $(GGS)_n$ linker, where n is an integer indicating the number of (GGS) repeats.

11. The method of claim 10, wherein n is greater than or equal to 3.

12. The method of claim 11, wherein n is 5.

13. The method of claim 8, wherein said flexible linker comprises a glycine-serine (GS)-rich linker.

14. The method of claim 13, wherein said flexible linker comprises a $(GGS)_n$ linker, where n is an integer indicating the number of (GGS) repeats.

15. The method of claim 14, wherein n is greater than or equal to 3.

16. The method of claim 15, wherein n is 5.

\* \* \* \* \*

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Sortase Recognition Sequence
<220> FEATURE:
<221> NAME/KEY: misc_feature
<222> LOCATION: (3)..(3)
<223> OTHER INFORMATION: Any amino acid residue

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 2

Leu Pro Lys Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 3

Leu Pro Ala Thr Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 4

Leu Pro Asn Thr Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 5

Leu Pro Glu Thr Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Sortase Recognition Sequence
<220> FEATURE:

```
<221> NAME/KEY: misc_feature
<222> LOCATION: (3)..(3)
<223> OTHER INFORMATION: Any amino acid residue

<400> SEQUENCE: 6

Leu Pro Xaa Ala Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 7

Leu Pro Asn Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Sortase Recognition Sequence
<220> FEATURE:
<221> NAME/KEY: misc_feature
<222> LOCATION: (3)..(3)
<223> OTHER INFORMATION: Any amino acid residue

<400> SEQUENCE: 8

Leu Pro Xaa Thr Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 9

Leu Pro Asn Thr Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Sortase Recognition Sequence
<220> FEATURE:
<221> NAME/KEY: misc_feature
<222> LOCATION: (3)..(3)
<223> OTHER INFORMATION: Any amino acid residue

<400> SEQUENCE: 10

Leu Gly Xaa Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 11
```

```
Leu Gly Ala Thr Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Sortase Recognition Sequence
<220> FEATURE:
<221> NAME/KEY: misc_feature
<222> LOCATION: (3)..(3)
<223> OTHER INFORMATION: Any amino acid residue

<400> SEQUENCE: 12

Ile Pro Xaa Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 13

Ile Pro Asn Thr Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Sortase Recognition Sequence

<400> SEQUENCE: 14

Ile Pro Glu Thr Gly
1               5
```